United States Patent [19]

Lunn et al.

[11] 4,048,161
[45] Sept. 13, 1977

[54] 7-[α-(BENZIMIDAZOL-2-YLCARBONYLAMINO)-ARYLACETAMIDO]CEPHALOSPORINS

[75] Inventors: William H. W. Lunn; Edward V. Mason, both of Indianapolis, Ind.

[73] Assignee: Eli Lilly and Company, Indianapolis, Ind.

[21] Appl. No.: 687,976

[22] Filed: May 20, 1976

[51] Int. Cl.$^2$ .......................................... C07D 501/20
[52] U.S. Cl. ..................................... 544/27; 424/246; 544/28
[58] Field of Search ................................... 260/243 C

[56] References Cited
U.S. PATENT DOCUMENTS 3,867,380  2/1975  Dunn et al. ...................... 260/243 C Primary Examiner—Nicholas S. Rizzo
Attorney, Agent, or Firm—William C. Martens, Jr.; Everet F. Smith

[57] ABSTRACT

Cephalosporin antibiotics of the formula

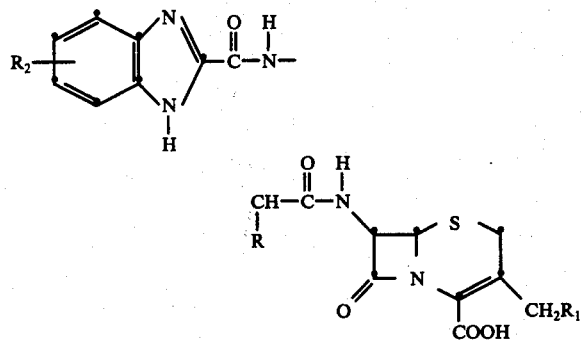

in which, for example, R is phenyl, hydroxyphenyl, halophenyl, thienyl, or furyl; $R_1$ is hydrogen, carbamoyloxy, acetoxy, a lower alkyl substituted 1H-tetrazol-5-ylthio or 1,3,4-thiadiazol-5-ylthio group; and $R_2$ is hydrogen, $C_1$-$C_3$ alkyl, $C_1$-$C_3$ alkoxy, chloro, bromo, or fluoro; are highly active broad spectrum antibiotics especially useful in the treatment of infections attributable to the gram-negative microorganisms.

16 Claims, No Drawings

7-[α-(BENZIMIDAZOL-2-YLCARBONYLAMINO)-ARYLACETAMIDO]CEPHALOSPORINS

BACKGROUND OF THE INVENTION

Cephalosporin compounds having a substituted amino group in the α-position of the 7-acylamido side chain have been described in the literature. In U.S. Pat. Nos. 3,673,183 and 3,708,479, α-ureido cephalosporanic acids are disclosed. Penicillins and cephalosporins having an α-(3-imidoylureido) arylacetamido side chain are described in U.S. Pat. Nos. 3,634,405 and 3,646,024, respectively. In U.S. Pat. No. 3,687,949, cephalosporins having an α-(3-acylureido) arylacetamido side chain are disclosed. This latter patent defines a wide variety of acyl groups attached to the terminal nitrogen of the α-ureido group of the 7-arylacetamido side chain. Also, in U.S. Pat. No. 3,579,514, cephalosporins having an α-(3-guanyl-1-ureido) arylacetamido side chain are described.

A new class of cephalosporin compounds having a substituted carbamido substituent in the α-position of the 7-arylacetamido side chain has now been discovered. This class of compounds represents the basis of this invention. These compounds, having a high level of activity against both gram-negative and gram-positive pathogens, are prepared by acylating the free amino group in the 7-position side chain of a cephalosporin including, for example, cephaloglycin, 7-(D-α-amino-α-phenylacetamido) -3-(1-lower alkyl-1H-tetrazol-5-ylthiomethyl) -3-cephem-4-carboxylic acid, 7-(D-α-amino-α-phenylacetamido)-3-(5-lower alkyl-1,3,4-thiadiazol-2-ylthiomethyl)-3-cephem-4-carboxylic acid, and the like, as well as hydroxy and halogen derivatives thereof with an appropriately structured acylating agent.

SUMMARY OF THE INVENTION

Thus, this invention is directed to a compound of the formula

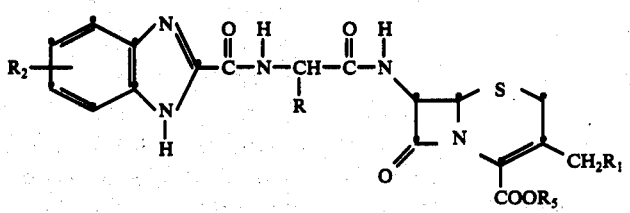

in which R is phenyl, monohydroxyphenyl, dihydroxyphenyl, monohalophenyl, monohydroxy substituted monohalophenyl, thienyl, or furyl;

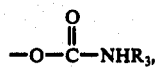

$R_1$ is hydrogen, acetoxy,

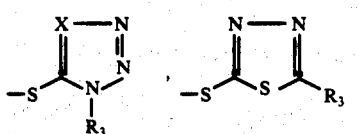

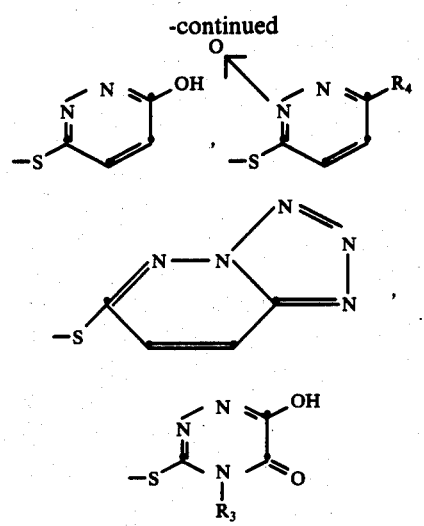

in which, in any of the above, X is =CH— or =N—, $R_3$ is hydrogen or $C_1$-$C_4$ alkyl, and $R_4$ is methyl, methoxy, or chloro;

$R_2$ is hydrogen, $C_1$-$C_3$ alkyl, $C_1$-$C_3$ alkoxy, chloro, bromo, or fluoro; and $R_5$ is hydrogen, indanyl, phthalidyl, an acyloxymethyl group of the formula

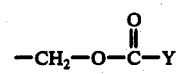

in which Y is $C_1$-$C_4$ alkyl or phenyl, or, when $R_5$ is hydrogen, the pharmaceutically acceptable non-toxic salts thereof.

The new cephalosporins described and claimed herein are active against a broad spectrum of microorganisms, and, accordingly, are useful for combating infections in warm-blooded animals. Administration generally is by the parenteral route.

Furthermore, the cephalosporis described herein include biologically active esters, for example, the acetoxymethyl or the benzoyloxymethl esters, and also include pharmaceutically useful salts, particularly the alkali metal salts, such as the lithium, sodium, and potassium salts.

DETAILED DESCRIPTION OF THE INVENTION

As indicated above, this invention relates to new cephalosporin antibiotic compounds having the following general formula I (I)

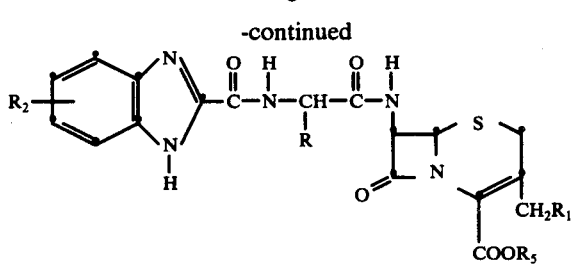

in which R, $R_1$, $R_2$, and $R_5$ are as aforedescribed.

$R_2$ above is defined as hydrogen, $C_1$-$C_3$ alkyl, $C_1$-$C_3$ alkoxy, chloro, bromo, or fluoro. Examples of these substituents are hydrogen, methyl, ethyl, n-propyl, isopropyl, methoxy, ethoxy, n-propoxy, isopropoxy, chloro, bromo, and fluoro. Preferably, $R_2$ is hydrogen, methyl, methoxy, chloro, or fluoro, and, most preferably, $R_2$ is hydrogen.

In the foregoing definition, the substituted α-amino moiety has the formula

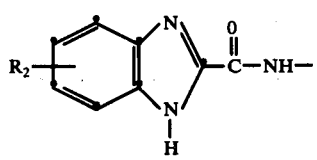

Examples of this moiety are benzimidazol-2-ylcarbonylamino-, 4-methylbenzimidazol-2-ylcarbonylamino-, 5-ethylbenzimidazol-2-ylcarbonylamino-, 4-n-propylbenzimidazol-2-ylcarbonylamino-, 4-methoxybenzimidazol-2-ylcarbonylamino-, 5-ethoxybenzimidazol-2-ylcarbonylamino-, 4-isopropoxybenzimidazol-2-ylcarbonylamino-, 4-chlorobenzimidazol-2-ylcar-bonylamino-, 5-fluorobenzimidazol-2-ylcarbonylamino-, 4-bromobenzimidazol-2-ylcarbonylamino-, 5-isopropylbenz- imidazol-2-ylcarbonylamino-, and the like.

The group R of the compounds of this invention is phenyl, monohydroxphenyl, dihydroxyphenyl, monohalophenyl, monohydroxy substituted monohalophenyl, thienyl, or furyl. The term "halo" as used herein refers to fluoro, chloro, and bromo, and, preferably, to chloro. Representative examples of the group R are phenyl, 3-hydroxyphenyl, 4-hydroxyphenyl, 3,5-dihydroxphenyl, 4-chlorophenyl, 4bromophenyl, 3-fluoro-phenyl, 2-chlorophenyl, 2-hydroxyphenyl, 3-chloro-4-hydroxy-phenyl, 3-hydroxy-4-bromophenyl, 3-fluoro-4hydroxyphenyl, 2-thienyl, 3-thienyl, 2-furyl, 3-furyl, and the like. Preferably, R is phenyl, p-hydroxyphenyl, or 2-thienyl, and, most preferably, R is p-hydroxyphenyl.

The novel cephalosporin compounds represented by the general formula I have in the 3-position a substituent of the formula —$CH_2R_1$ in which $R_1$ is hydrogen, acetoxy, N-alkyl substituted and unsubstituted carbamoyloxy, or any of a group of specific heterocyc- lylthio substituents.

The following therefore are illustrative of a portion of the group —$CH_2R_1$ in formula I above: methyl, acetoxymethyl, carbamoyloxymethyl, N-methylcarbamoyloxy-methyl, N-ethylcarbamoyloxymethyl, N-n-propylcarbamoyloxy-methyl, N-isopropylcarbamoyloxymethyl, N-n-butylcarbamoyl-oxymethyl, N-isobutylcarbamoyloxymethyl, and the like.

In addition, the 3-substituent of the cephalosporins of this invention is selected from a group of specifically structured heterocyclylthiomethyl moieties.

Included among these are IH-unsubstituted and substituted tetrazol-5-ylthiomethyl groups of the formula

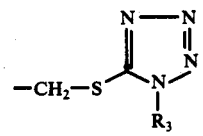

Specifically, these include tetrazol-5-ylthiomethyl, 1-methylteetrazol-5-ylthiomethyl, 1-ethyltetrazol-5-ylthiomethyl, 1-n-propyltetrazol-5-ylthiomethyl, 1-isopropyltetrazol-5-ylyhiomethyl, 1-n-butyltetrazol-5-ylthiomethyl, 1-isobutyl-tetrazol-5-ylthiomethyl, and the like.

Another class of these substituents includes 1-unsubstituted and substituted 1,2,3-triazol-5-ylthiomethyl groups of the formula.

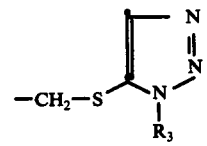

Illustrative of this class are 1,2,3-triazol-5-ylthiomethyl, 1-methyl-1,2,3-triazol-5-ylthiomethyl,1-ethyl-1,2,3-triazol-5-ylthiomethyl, 1-n-propyl-1,2,3-triazol-5-ylthiomethyl, 1-isopropyl-1,2,3-triazol-5-ylthiomethyl, 1-n-butyl-1,2,3-triazol-5-ylthiomethyl, 1-isobutyl-1,2,3-triazol-5-ylthiomethyl, and the like.

Another class of these substituents includes 5-unsubstituted or substituted 1,3,4-thiadiazol-2-ylthiomethyl groups of the formula

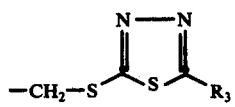

Illustrative groups of this class are 1,3,4-thiadiazol-2-ylthiomethyl, 5-methyl-1,3,4-thiadiazol-2-ylthiomethyl, 5-ethyl-1,3,4-thiadiazol-2-ylthiomethyl, 5-n-propyl-1,3,4-thiadiazol-2-ylthiomethyl, 5-isopropyl-1,3,4-thiadiazol-2-ylthiomethyl, 5-isobutyl-1,3,4-thiadiazol-2-ylthiomethyl, 5-sec-butyl-1,3,4-thiadiazol-2-ylthiomethyl, and the like.

Another such group is 3-hydroxypyridazin-6-ylthiomethyl, which has the formula

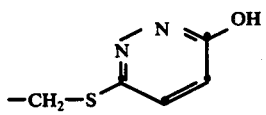

This particular substituent is disclosed in U.S. Pat. No. 3,813,376.

A further substituent is a 1-oxide-3-substituted-pyridazin-6-ylthiomethyl having the formula

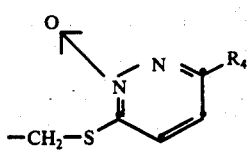

These particular substituents are disclosed in U.S. Pat. No. 3,892,737, and include 1-oxide-3-methylpyridazin-6-ylthiomethyl, 1-oxide-3-methoxypyridazin-6-ylthiomethyl, and 1-oxide-3-chloro-pyridazin-6-ylthiomethyl.

Another such group is tetrazolo[4,5-b]pyridazin-6-ylthiomethyl having the formula

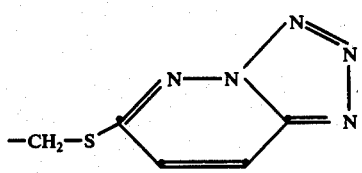

This substituent is disclosed in U.S. Pat. No. 3,814,755.

A final substituent is a 5-oxo-6-hydroxy-4,5-dihydro-1,2,4-triazin-3-ylthiomethyl having the formula

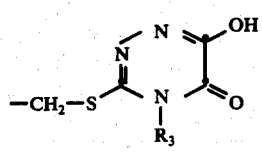

These substituents are described in co-pending application Ser. No. 583,924 filed June 10, 1975. The 3-mercapto-1,2,4-triazines which represent the source of these substituents are prepared by a method described in Pesson et al., *Bulletin de la Societe Chemique de France*, (1970), pages 1590–1599. They are illustrated by the following groups: 5-oxo-6-hydroxy-4,5-dihydro-1,2,4-triazin-3-ylthiomethyl; 4-methyl-5-oxo-6-hydroxy-4,5-dihydro-1,2,4-triazin-3-ylthiomethyl; 4-ethyl-5-oxo-6-hydroxy-4,5-dihydro-1,2,4-triazin-3-ylthiomethyl; 4-n-propyl-5-oxo-6-hydroxy-4,5-dihydro-1,2,4-triazin-3-ylthiomethyl; 4-isopropyl-5-oxo-6-hydroxy-4,5-dihydro-1,2,4-triazin-3-ylthiomethyl; 4-n-butyl-5-oxo-6-hydroxy-4,5-dihydro-1,2,4-triazin-3-ylthiomethyl; 4-sec-butyl-5-oxo-6-hydroxy-4,5-dihydro-1,2,4-triazin-3-ylthiomethyl; 4-isobutyl-5-oxo-6-hydroxy-4,5-dihydro-1,2,4-triazin-3-ylthiomethyl; and the like.

Preferably, the 3-substituents are selected from the group consisting of 1H-unsubstituted and substituted tetrazol-5-ylthiomethyl; 1-unsubstituted and substituted 1,2,3-triazol-5-ylthiomethyl; 5-unsubstituted and substituted 1,3,4-thiadiazol-2-ylthiomethyl; and 4-unsubstituted and substituted 5-oxo-6-hydroxy-4,5-dihydro-1,2,4-triazin-3-ylthiomethyl. Of the above, the group $R_3$ preferably is hydrogen or methyl, and, most preferably, is methyl.

The compounds of this invention are prepared by acylation of the appropriate 7-(D-α-amino-α-arylacetamido)-3-cephem-4-carboxylic acid. This cephalosporin has the structure

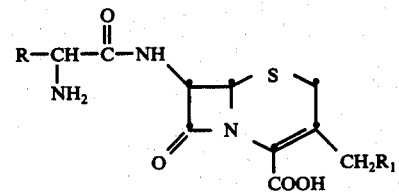

(II)

in which R and $R_1$ are as aforedescribed.

The reagent used to achieve acylation of the above cephalosporin and thus preparation of the compounds of this invention is prepared from o-phenylenediamine or an appropriately substituted o-phenylenediamine. Preparation of a suitable acylating agent is depicted by the following sequence:

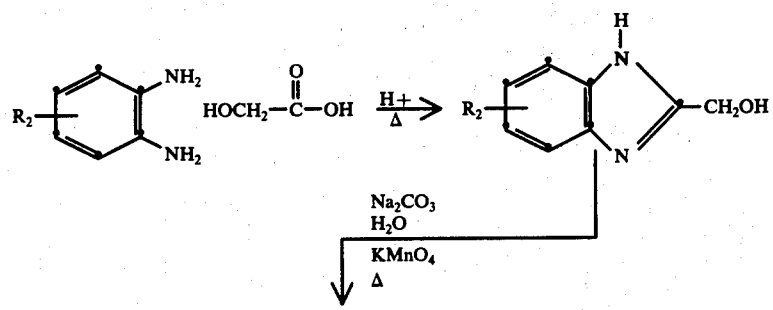

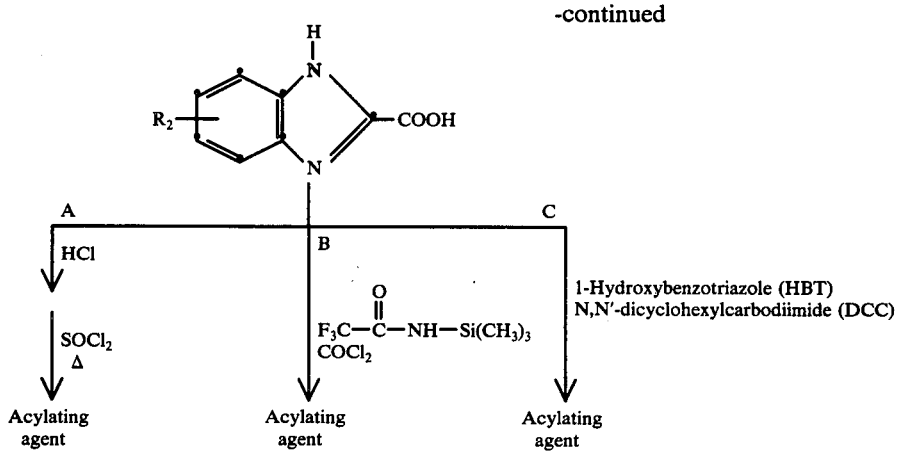

In the foregoing sequence, the selected o-phenylenediamine is dissolved in dilute aqueous hydrochloric acid, and at least an equimolar quantity of glycolic acid is added. The mixture is allowed to react at an elevated temperature, and the product, the corresponding 2-hydroxymethylbenzimidazole, is recovered by neutralization of the acidic medium.

The resulting 2-hydroxymethylbenzimidazole then is oxidized in the presence of a suitable oxidizing agent, typically potassium permanganate. This reaction is carried out under moderately basic conditions, and, upon completion of the reaction, the product is recovered by acidification of the reaction mixture.

The 2-benzimidazolecarboxylic acid which results from the aforedescribed sequence constitutes structurally the acyl moiety which is intended to displace a hydrogen on the α-amino substituent and thereby to produce a compound of this invention. However, the 2-benzimidazolecarboxylic acid itself is not suitable for use in achieving the intended acylation reaction. The acid must be converted to a form which has been sufficiently activated to effect the desired conversion. Any of three procedures are available to accomplish activation of the 2-benzimidazolecarboxylic acid.

The first reaction is that designated by Route A in the foregoing sequence. This reaction is described by Copeland and Day, *Journal of the American Chemical Society*, 65, 1072 (1943). It involves treatment of the hydrochloride salt of the 2-benzimidazolecarboxylic acid with thionyl chloride at an elevated temperature. The literature designates the product which results as a dimer of the 2-benzimidazolecarboxylic acid starting material formed by loss of a molecule of water for each molecule of the 2-benzimidazolecarboxylic acid. Thus, when 2-benzimidazolecarboxylic acid itself is employed in the activation reaction, the product is stated to be dibenzimidazo-(1,2-a,1′,2′-d)-tetrahydropyrazine-6,13-dione, that is, a compound having the following structure

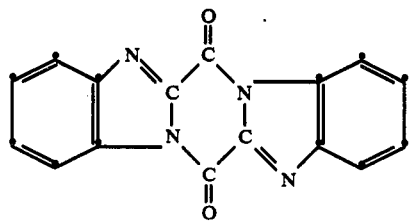

The method of Route B depicted in the sequence provided hereinabove involves treatemnt of the 2-benzimidazolecarboxylic acid with a silylating agent, typically an agent which affords a trimethylsilyl moiety and thus converts the 2-benzimidazolecarboxylic acid to the corresponding trimethylsilyl derivative. This product then is treated with phosgene to produce a product which is of undetermined structure but which exhibits characteristics suitable for accomplishing acylation of the 7-α-aminoarylacetamidocephalosporin.

The method of Route C depicted in the sequence provided hereinabove involves treatment of the 2-benzimidazolecarboxylic acid with 1-hydroxybenzotriazole (HBT) and N,N′-dicyclohexylcarbodiimide (DDC). The reaction is carried out in a suitable solvent and at a temperature generally from about −10° C. to about +25° C., and preferably at about 20°–25° C. The product is the ester formed from HBT and the 2-benzimidazolecarboxylic acid. This ester represents an activated form of the 2-benzimidazolecarboxylic acid and is useful in carrying out the intended acylation reaction. The resulting ester need not be isolated prior to use. Instead, the reaction mixture containing the active ester product generally is filtered, and the filtrate itself is employed in the acylation reaction.

As indicated hereinabove, the compounds of this invention are prepared by reacting a compound of formula II with the appropriate acylating agent. The starting materials represented by formula II are available by conversion of a 7-amino cephalosporin of the formula

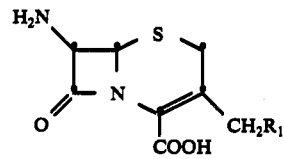

In general, the 7-amino compound can be reacted with the anhydride formed from an α-(t-butyloxycarbamido)arylacetic acid of the formula

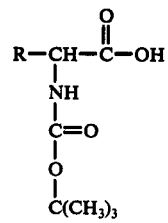

and isobutyl chloroformate. Following the acylation, the t-butyloxcarbonyl protecting group is removed by known methods, for example, by treatment with trifluoroacetic acid in the cold, or, alternatively, by treatment with p-toluenesulfonic acid in acetonitrile.

The product, a compound of formula II, then is reacted with the hereinbefore described acylating agent to effect acylation of the free α-amino group in the 7-position side chain. This acylation is carried out in an inert solvent and at a temperature generally from about −5° C. to about 30° C. Solvents such as acetonitrile, tetrahydrofuran, N,N-dimethylformamide, and N,N-dimethylacetamide can be used in the acylation reaction. A preferred solvent is tetrahydrofuran (THF). In the event that the cephalosporin starting material is insoluble or is only partially soluble in the solvent, it can be solubilized by addition of a silylating agent such as N,O-bis-(trimethylsilyl)acetamide (BSA), N-trimethylsilylacetamide (MSA), and the like. In the event that such a silylating agent is employed, the celphalosporin will be converted to its trimethylsilyl ester and thus will be solubilized prior to reaction with the acylating agent.

A hydrogen halide acceptor preferably is included in those acylation reactions in which the acylating agent which is employed results from the method of Route B described hereinabove. Hydrogen halide acceptors which can be employed include teritary amines sush as treithylamine and pyridine, as well as alkylene oxides such as propylene oxide or butylene oxide. Preferably, propylene oxide is employed.

By the above methods, the free acid cephalosporins of this invention, that is, those in which $R_5$ is hydrogen, are prepared.

The compounds of this invention, in their free acid from ($R_5 =$ H), form pharmaceutically acceptable salts with inorganic bases such as the alkali metal carbonates and bicarbonates. For example, the lithium, sodium, and potassium salts can be formed from lithium, sodium, and potassium carbonate, respectively, by conventional procedures.

The cephalosporin antibiotics of this invention in the form of their free acid or their alkali metal salts can be converted to their corresponding biologically active esters. These are compounds in which $R_5$ is indanyl, phthalidyl

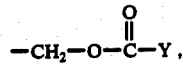

in which Y is $C_1$-$C_4$ alkyl or phenyl. The biologically active esters in which $R_5$ is

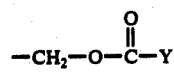

are prepared by reacting an alkali metal salt of the free acid cephalosporin, for example, the lithium, sodium, or potassium salt, with an acyloxymethyl halide of the formula

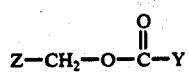

in which Z is chloro or bromo and Y is $C_1$-$C_4$ alkyl or phenyl. Acyloxymethyl halides which can be employed include chloromethyl acetate, bromomethyl acetate, bromomethyl propionate, chloromethyl pivaloate, chloromethyl benzoate, and the like.

Preparation of the acyloxymethyl esters is carried out by reacting the alkali metal salt form of the cephalosporin acid in an inert solvent with at least a molar equivalent of the bromomethyl or the chloromethyl ester, for example, bromomethyl acetate, at room temperature or at a slightly elevated temperature up to about 40°–45° C. A solvent such as acetone, tetrahydrofuran, dioxane, N,N-dimethylformamide, methylene chloride, and the like, can be used.

The indanyl ester compounds of this invention are those in which $R_5$ is

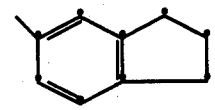

These are prepared by reacting 5-indanol in an inert solvent such as dioxane or tetrahydrofuran with the free acid form of a cephalosporin of this invention in the presence of a condensing agent such as diimide, for example, N,N'-dicyclohexylcarbodiimide. The reaction is carried out with stirring at about 20°–35° C. for about six to about eight hours. The indanyl ester is isolated by diluting the reaction mixture with water and then filtering it to remove the insoluble dicyclohexylurea. The ester then is extracted from the filtrate.

Alternatively, the indanyl ester can be prepared by reacting the mixed acid anhydride formed from the free acid cephalosporin and acetic acid with 5-indanol.

Phthalidyl ester compounds of this invention are those in which the group $R_5$ is

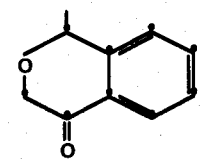

These are obtained by reacting bromophthalide having the formula

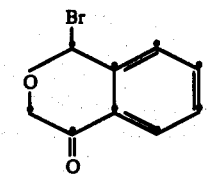

with a salt of the free acid cephalosporin. This esterification can be carried out in N,N-dimethylformamide, N,N-dimethylacetamide, dioxane, tetrahydrofuran, or mixtures thereof, by slowly warming a mixture of equimolar amounts of the cephalosporin salt, for example, the sodium or the potassium salt, and bromophthalide.

Illustrative of the compounds of this invention are the following:

7-[α-(benzimidazol-2-ylcarbonylamino) phenylacetamido]-3-methyl-3-cephem-4-carboxylic acid;

7-[α-(benzimidazol-2-ylcarbonylamino)- phenylacetamido]-3-acetoxymethyl-3-cephem-4-carboxylic acid;

7-[α-(benzimidazol-2-ylcarbonylamino)-phenylacetamido]-3-carbamoyloxymethyl-3-cephem-4-carboxylic acid;

7-[α-(benzimidazol-2-ylcarbonylamino)-phenylacetamido]-3-(N-methylcarbamoyloxymethyl)-3-cephem-4-carboxylic acid;

7-[α-(benzimidazol-2-ylcarbonylamino)-phenylacetamido]-3-(tetrazol-5-ylthiomethyl)-3-cephem-4-carboxylic acid;

7-[α-(benzimidazol-2-ylcarbonylamino)-phenylacetamido]-3-(1-methyltetrazol-5-ylthiomethyl)-3-cephem-4-carboxylic acid;

7-[α-(benzimidazol-2-ylcarbonylamino)-phenylacetamido]-3-(1-ethyltetrazol-5-ylthiomethyl)-3-cephem-4-carboxylic acid;

7-[α-(benzimidazol-2-ylcarbonylamino)-phenylacetamido]-3-(1-isopropyltetrazol-5-ylthiomethyl)-3-cephem-4-carboxylic acid;

7-[α-(benzimidazol-2-ylcarbonylamino)-phenylacetamido]-3-(1,2,3-triazol-5-ylthiomethyl)-3-cephem-4-carboxylic acid;

7-[α-(benzimidazol-2-ylcarbonylamino)-phenylacetamido]-3-(1-methyl-1,2,3-triazol-5-ylthiomethyl)-3-cephem-4-carboxylic acid;

7-[α-(benzimidazol-2-ylcarbonylamino)-phenylacetamido]-3-(1-ethyl-1,2,3-triazol-5-ylthiomethyl)-3-cephem-4-carboxylic acid;

7-[α-(benzimidazol-2-ylcarbonylamino)-phenylacetamido]-3-(1-n-butyl-1,2,3-triazol-5-ylthiomethyl)-3-cephem-4-carboxylic acid;

7-[α-(benzimidazol-2-ylcarbonylamino)-phenylacetamido]-3-(1,3,4-thiadiazol-2-ylthiomethyl)-3-cephem-4-carboxylic acid;

7-[α-(benzimidazol-2-ylcarbonylamino)-phenylacetamido]-3-(5-methyl-1,3,4-thiadiazol-2ylthiomethyl)-3-cephem-4-carboxylic acid;

7-[α-(benzimidazol-2-ylcarbonylamino)-phenylacetamido]-3-(5-ethyl-1,3,4-thiadiazol-2-ylthiomethyl)-3-cephem-4-carboxylic acid; 7-[α-(benzimidazol-2-ylcarbonylamino)phenylacetamido]-3-(5-n-propyl-1,3,4-thiadiazol-2-ylthiomethyl)-3-cephem-4-carboxylic acid;

7-[α-(benzimidazol-2-ylcarbonylamino)-phenylacetamido]-3-(3-hydroxypyridazin-6-ylthiomethyl)-3-cephem-4-carboxylic acid;

7-[α-(benzimidazol-2-ylcarbonylamino)-phenylacetamido]-3-(1-oxide-3-methylpyridazin-6-ylthiomethyl)-3-cephem-4-carboxylic acid;

7-[α-(benzimidazol-2-ylcarbonylamino)-phenylacetamido]-3-(1-oxide-3-methoxypyridazin-6-ylthiomethyl)-3-cephem-4-carboxylic acid;

7-[α-(benzimidazol-2-ylcarbonylamino)-phenylacetamido]-3-(1-oxide-3-chloropyridazin-6-ylthiomethyl)-3-cephem-4-carboxylic acid;

7-[α-(benzimidazol-2-ylcarbonylamino)-phenylacetamido]-3-(tetrazolo-[4,5-b]pyridazin-6-ylthiomethyl)-3-cephem-4-carboxylic acid;

7-[α-(benzimidazol-2-ylcarbonylamino)-phenylacetamido]-3-(5-oxo-6-hydroxy-4,5-dihydro-1,2,4-triazin-3-ylthiomethyl)-3-cephem-4-carboxylic acid;

7-[α-(benzimidazol-2-ylcarbonylamino)-phenylacetamido]-3-(4-methyl-5-oxo-6-hydroxy-4,5-dihydro-1,2,4-triazin-3-ylthiomethyl)-3-cephem-4-carboxylic acid;

7-[α-(benzimidazol-2-ylcarbonylamino)-phenylacetamido]-3-(4-ethyl-5-oxo-6-hydroxy-4,5-dihydro-1,2,4-triazin-3-ylthiomethyl)-3-cephem-4-carboxylic acid;

7-[α-(benzimidazol-2-ylcarbonylamino)-phenylacetamido]-3-(4-isobutyl-5-oxo-6-hydroxy-4,5-dihydro-1,2,4-triazin-3-ylthiomethyl)-3-cephem-4-carboxylic acid;

7-[α-(benzimidazol-2-ylcarbonylamino)-4-hydroxyphenylacetamido]-3-carbamoyloxymethyl-3-cephem-4-carboxylic acid;

7-[α-(benzimidazol-2-ylcarbonylamino)-4-hydroxyphenylacetamido]-3-(1-methyl-1,2,3-triazol-5-ylthiomethyl)-3-cephem-4-carboxylic acid;

7-[α-(benzimidazol-2-ylcarbonylamino)-4-hydroxyphenylacetamido]-3-(1-methyltetrazol-5-ylthiomethyl)-3-cephem-4-carboxylic acid;

7-[α-(benzimidazol-2-ylcarbonylamino)-4-hydroxyphenylacetamido]-3-(5-methyl-1,3,4-thiadiazol-2-ylthiomethyl)-3-cephem-4-carboxylic acid;

7-[α-(benzimidazol-2-ylcarbonylamino)-4-hydroxyphenylacetamido]-3-(4-methyl-5-oxo-6-hydroxy-4,5-dihydro-1,2,4-triazin-3-ylthiomethyl)-3-cephem-4-carboxylic acid;

7-[α-(5-methylbenzimidazol-2-ylcarbonylamino)-phenylacetamido]-3-acetoxymethyl-3-cephem-4-carboxylic acid;

7-[α-(4-ethylbenzimidazol-2-ylcarbonylamino)phenylacetamido]-3-(5-methyl-1,3,4-thiadiazol-2-ylthiomethyl)-3-cephem-4-carboxylic acid;

7-[α-(5-methoxybenzimidazol-2-ylcarbonylamino)phenylacetamido]-3-methyl-3-cephem-4-carboxylic acid;

7-[α-(4-fluorobenzimidazol-2-ylcarbonylamino)phenylacetamido]-3-carbamoyloxymethyl-3-cephem-4-carboxylic acid;

7-[α-(5-chlorobenzimidazol-2-ylcarbonylamino)phenylacetamido]-3-(N-ethylcarbamoyloxymethyl)-3-cephem-4-carboxylic acid;

7-[α-(benzimidazol-2-ylcarbonylamino)-3-hydroxyphenylacetamido]-3-(1-methyltetrazol-5-ylthiomethyl)-3-cephem-4-carboxylic acid;

7-[α-(benzimidazol-2-ylcarbonylamino)-3-chlorophenylacetamido]-3-(4-methyl-5-oxo-6-hydroxy-4,5-dihydro-1,2, 4-triazin-3-ylthiomethyl)-3-cephem-4-carboxylic acid;

7-[α-(benzimidazol-2-ylcarbonylamino)-2,4-dihydroxyphenylacetamido]-3-(1,3,4-thiadiazol-2-ylthiomethyl)-3-cephem-4-carboxylic acid;

7-[α-(benzimidazol-2-ylcarbonylamino)-3-chloro-4-hydroxyphenylacetamido]-3-(1-methyl-1,2,3-triazol-5-ylthiomethyl)-3-cephem-4-carboxylic acid;

7-[α-(benzimidazol-2-ylcarbonylamino)-2-thienylacetamido]-3-(5-methyl-1,3,4-thiadiazol-2-ylthiomethyl)-3-cephem-4carboxylic acid;

7-[α-(benzimidazol-2-ylcarbonylamino)-3-thienylacetamido]-3-(1-methyltetrazol-5-ylthiomethyl)-3-cephem-4-carboxylic acid;

7-[α-(benzimidazol-2-ylcarbonylamino)-2-furylacetamido]-3-carbamoyloxymethyl-3-cephem-4-carboxylic acid;

7-[α-(benzimidazol-2ylcarbonylamino)-3-furylacetamido]-3-acetoxymethyl-3-cephem-4-carboxylic acid;

7-[α-(4-methylbenzimidazol-2-ylcarbonylamino)-2-thienylacetamido]-3-(1-methyltetrazol-5-ylthiomethyl)-3-cephem-4-carboxylic acid;

7-[α-(4-ethoxybenzimidazol-2-ylcarbonylamino)-4-hydroxyphenylacetamido]-3-(4-ethyl-5-oxo-6-hydroxy- 4,5-dihydro-1,2,4-triazin-3-ylthiomethyl)-3-cephem-4-carboxylic acid;

7-[α-(5-bromobenzimidazol-2-ylcarbonylamino)-3,5-dihydroxyphenylacetamido]-3-(1-ethyltetrazol-5-ylthiomethyl)-3-cephem-4-carboxylic acid;

7-[α-(4-isopropoxybenzimidazol-2-ylcarbonylamino)-3-hydroxy-4-fluorophenylacetamido]-3-methyl-3-cephem-4-carboxylic acid;

7-[α-(5-n-propylbenzimidazol-2-ylcarbonylamino)-2-fluorophenylacetamido]-3-(1-n-butyl-1,2,3-triazol-5-ylthiomethyl)-3-cephem-4-carboxylic acid; and the like.

For the sake of conciseness, the above compounds are described in the form of their free acids. It is evident that these compounds are provided for the purpose of illustration only, and, moreover, that they likewise can be in the form of their pharmaceutically acceptable salts or their biologically active esters.

The cephalosporin antibiotics of this invention are highly effective in inhibiting the growth of a wide spectrum of pathogenic microorganisms of both the gram-positive and the gram-negative type.

The antibiotic activity of the cephalosporin compounds of this invention is illustrated by the data provided in the following Table of representative compounds. The values in the Table are the minimum inhibitory concentrations (MIC) for the test compounds against the indicated microorganisms. The MIC values were obtained using the gradient plate in vitro method for determining antibiotic activity.

parenterally in non-toxic doses of from about 10 to about 500 mg/kg. body weight. The biologically active ester compounds of this invention are useful antibiotics when administered orally in non-toxic doses of from about 50 to about 750 mg/kg. body weight.

The following are provided as specific illustrations of the preparation of the acylating agent which is employed in preparing the compounds of this invention.

A. Preparation of 2-Hydroxymethylbenzimidazole

To 150 ml. of 4N hydrochloric acid were added 10.8 gms. (100 mmoles.) of o-phenylenediamine and 11.4 gms. (150 mmoles.) of glycolic acid. The mixture was refluxed for 40 minutes. The solution then was cooled, filtered, and neutralized by the addition of concentrated ammonium hydroxide. The title compound precipitated and was filtered and dried to obtain 4 gms. of product.

B. Preparation of 2-Benzimidazolecarboxylic Acid

The 2-hydroxymethylbenzimidazole from Part A (4 gms.) was refluxed in a small amount of saturated sodium carbonate solution with addition of sufficient boiling water to dissolve it. A hot, dilute solution of 6.67 gms. of potassium permanganate then was added slowly with stirring. Upon completion of the addition, the resulting suspension was refluxed for 30 minutes. The resulting hot liquid was separated by filtration from manganese dioxide which had formed. The filtrate then was cooled and rendered acidic (pH 5.0) by addition of

TABLE

ANTIBIOTIC ACTIVITY OF BENZIMIDAZOL-2-YLCARBONYLAMINO-SUBSTITUTED CEPHALOSPORINS

| | Minimum Inhibitory Concentration (mcg./ml.) Test Compound[2] | | | | | | |
|---|---|---|---|---|---|---|---|
| Test Organism[1] | A | B | C | D | E | F | G |
| Shigella sp. | 15 | 5.0 | 5.5 | 4.0 | 10 | 19.5 | 6.7 |
| Escherichia coli | 26.5 | 18.5 | 7.5 | 7.0 | 16 | 55 | 11.0 |
| Klebsiella pneumoniae | 18.5 | 5.0 | 0.9 | 0.6 | 4.5 | 10.0 | 1.0 |
| Aerobacter aerogenes | 18.3 | 8.5 | 13 | 10.0 | 21.5 | 55 | 19.2 |
| Salmonella heidelberg | 22 | 6.5 | 8.0 | 7.5 | 16 | 19.5 | 8.5 |
| Pseudomonas aeruginosa | 25 | 22 | 10.5 | 14.8 | 18.5 | 19.5 | 60 |
| Serratia marcescens | 100 | 21.5 | 20.7 | 14.8 | 70 | >200 | 41 |
| V41 | 4.0 | 5.0 | 0.9 | 0.6 | 4.0 | 0.9 | 0.8 |
| V32 | 5.0 | 7.0 | 0.9 | 0.6 | 5.0 | 0.9 | 1.8 |
| X400 | >20 | >20 | 60 | 19.5 | 100 | 120 | >200 |
| V84 | 0.6 | 0.7 | 0.8 | 0.5 | 1.0 | 0.8 | 0.8 |

Footnotes.
1. Test organisms V41, V32, and V84 are penicillin resistant *Staphylococcus*. X-400 is a methicillin resistant *Staphylococcus*.
2. Test Compounds:
    A. 7-[α-(benzimidazol-2-ylcarbonylamino)phenylacetamido]-3-acetoxymethyl-3-cephem-4-carboxylic acid.
    B. 7-[α-(benzimidazol-2-ylcarbonylamino)phenylacetamido]-3-(1-methyltetrazol-5-ylthiomethyl)-3-cephem-4-carboxylic acid.
    C. 7-[α-(benzimidazol-2-ylcarbonylamino)-4-hydroxyphenylacetamido]-3-(1-methyltetrazol-5-ylthiomethyl)-3-cephem-4-carboxylic acid.
    D. 7-[α-(benzimidazol-2-ylcarbonylamino)-2-thienylacetamido]-3-(1-methyltetrazol-5-ylthiomethyl)-3-cephem-4-carboxylic acid.
    E. 7-[α-(benzimidazol-2-ylcarbonylamino)-4-hydroxyphenylacetamido]-3-(5-methyl-1,3,4-thiadiazol-2-ylthiomethyl)-3-cephem-4-carboxylic acid.
    F. 7-[α-(benzimidazol-2-ylcarbonylamino)-4-hydroxyphenylacetamido]-3-carbamoyloxymethyl-3-cephem-4-carboxylic acid.
    G. 7-[α-benzimidazol-2-ylcarbonylamino)-4-hydroxyphenylacetamido]-3-(4-methyl-5-oxo-6-hydroxy-4,5-dihydro-1,2,4-triazin-3-ylthiomethyl)-3-4-carboxylic acid.

The cephalosporin antibiotics of this invention in which $R_5$ is hydrogen as well as the pharmaceutically acceptable salts thereof are useful in combatting infections in warm-blooded mammals when administered acetic acid. The resulting yellow precipitate was filtered, dried, and recrystallized from hot water to obtain 1.98 gms. of the title compound as fine yellow needles.

C. Conversion to the Acylating Agent by the Reaction of Route A

To 10 ml. of thionyl chloride were added 0.57 gms. of the hydrochloride salt of 2-benzimidazolecarboxylic acid. The mixture was stirred for 16 hours at about 75° C. The thionyl chloride then was filtered from the resulting yellow precipitate, and the precipitate was dried to obtain 0.388 gms. of product, postulated as dibenzimidazo-(1,2-a,1',2'-d)-tetrahydropyrazine-6,13-dione.

D. Conversion to the Acylating Agent by the Reaction of Route B

To 15 ml. of dry tetrahydrofuran (THF) were added 5.4 gms. (30 mmoles.) of 2-benzimidazolecarboxylic acid followed by 17.9 gms. (90 mmoles.) of N-trimethylsilyltrifluoromethylacetamide. The mixture was stirred for one hour at room temperature during which period a clear solution developed. The solution was cooled in an ice bath, and 25 ml. of a 1:1 mixture of phosgene and THF were added slowly by means of a syringe. The resulting mixture was stirred for 30 minutes at ice bath temperature and then for one hour at room temperature. The solution then was cooled in dry ice-acetone and stirred for 30 minutes. The resulting precipitate was quickly filtered and was washed with a small amount of dry THF. The solid was partially dried on the filter paper and then was dried in a bell jar in vacuo to obtain 2.54 gms. of the acylating agent.

The following examples are provided for the purpose of illustrating the preparation of the compounds of this invention. They are not intended to be limiting upon the scope of the invention.

EXAMPLE 1

To 10 ml. of dried THF were added 220 mg. (0.5 mmoles.) of 7-($\alpha$-amino)phenylacetamido-3-acetoxymethyl-3-cephem-4-carboxylic acid followed by 0.48 ml. (2 mmoles.) of N,O-bis-(trimethylsilyl)acetamide. To the mixture then were added 90 mg. of the acylating agent prepared by the method of Route A described above. The resulting mixture was stirred for 2 hours at room temperature. Methanol then was added to the reaction mixture, and the total was filtered. The filtrate was evaporated to a residue of about 5 ml., and 100 ml. of a 1:1 mixture of ethyl acetate and water were added. The pH of the resulting mixture was raised to 7.0 by addition of aqueous sodium bicarbonate. The organic layer then was separated from the aqueous layer, and the pH of the aqueous layer was lowered to 2.0 by addition of 1N hydrochloric acid. The acidic layer was extracted with ethyl acetate, and the ethyl acetate extract was dried over magnesium sulfate, filtered, and evaporated to obtain 104 mg. of 7-[$\alpha$-(benzimidazol-2-ylcarbonylamino)phenylacetamido]-3-acetoxymethyl-3-cephem-4-carboxylic acid.

NMR (DMSOd$_6$) 2.05 (s, 3, CH$_3$ of acetoxy), 3.50 (s, 2, 2-CH$_2$) 4.92 (q, 2, CH$_2$ of acetoxymethyl), 5.15 (d, 1, 6$\alpha$-H), 5.92 (d, 1, benzylic H; and q, 1, 7$\alpha$-H); 7.40 (m, 5, phenyl of phenylacetamido); 7.65 (m, 4, phenyl of benzimidazole); and 8.87 and 9.58 ppm. (dd, each represents one amide H).

EXAMPLE 2

Employing the method of Example 1, 7-($\alpha$-amino)phenylacetamido-3-(1-methyltetrazol-5-ylthiomethyl)-3-cephem-4-carboxylic acid was reacted with the appropriate acylating agent in the presence of N,O-bis-trimethylsilylacetamide (BSA) to obtain 135 mg. of 7-[$\alpha$-(benzimidazol-2-ylcarbonylamino)-phenylacetamido]-3-(1-methyltetrazol-5-ylthiomethyl)-3-cepham-4-carboxylic acid.

NMR (DMSOd$_6$) 3.66 (s, 2, 2-CH$_2$); 3.93 (s, 3, tetrazole CH$_3$); 4.32 (s, 2, 3'-CH$_2$); 5.11 (d, 1, 6$\alpha$-H); 5.91 (d, 1, benzylic H: and q, 1, 7$\alpha$-H); 7.41 and 7.65 (m, 9, phenyls of phenylacetamido and benzimidazole); and 8.90 and 9.60 ppm. (dd, each represents one amide H).

EXAMPLE 3

To dry acetonitrile were added 477 mg. (1 mmole.) of 7-($\alpha$-amino-4-hydroxyphenylacetamido)-3-(1-methyltetrazol-5-ylthiomethyl)-3-cephem-4-carboxylic acid and 2 ml. of N,O-bis-trimethylsilylacetamide (BSA). The mixture was stirred for one hour after which time solution was complete. The acetonitrile then was evaporated from the mixture, and 50 ml. of dry THF were added. The resulting THF solution was cooled in an ice bath, and 1 ml. of propylene oxide was added followed by 246 mg. (1.1 mmoles.) of the acylating agent prepared by the method of Route B described hereinabove. The resulting mixture was warmed to room temperature and was stirred for two hours. Methanol (2 ml.) then was added; however, no precipitate formed. The solution then was evporated to about 10 ml., and the residue was slowly dropped into stirring ice water. After 10 minutes of stirring, the resulting suspension was filtered, and the solid was dried. The solid then was triturated with ethyl ether, and the ether solubles were discarded. The remaining residual solid was dissolved in ethyl acetate, and the insoluble portion was removed by filtration. The filtrate then was evaporated to obtain 141 mg. of a first crop and 62 mg. of a second crop of 7-[$\alpha$-(benzimidazol-2-ylcarbonylamino)-4-hydroxyphenylacetamido]-3-(1-methyltetrazol-5-ylthiomethyl)-3-cephem-4-carboxylic acid as a crystalline solid.

NMR (DMSOd$_6$ and D$_2$O) 3.66 (s, 2, 2-CH$_2$), 3.98 (s, 3, tetrazole CH$_3$), 5.13 (d, 1, 6$\alpha$-H), 5.81 (s, 1, benzylic H; and d, 1, 7$\alpha$-H), 7.23 (q, 4, aromatic H of p-hydroxyphenyl), and 7.65 ppm. (m, 4, aromatic H of benzimidazole).

EXAMPLE 4

Employing the method described in Example 3, 467 mg. (1 mmole.) of 7-($\alpha$-amino-2-thienylacetamido)-3-(1-methyltetrazol-5-ylthiomethyl)-3-cephem-4-carboxylic acid was acylated to obtain 258 mg. of 7-[$\alpha$-(benzimidazol-2-ylcarbonylamino)-2-thienylacetamido]-3-(1-methyltetrazol-5-ylthiomethyl)-3-cephem-4-carboxylic acid. A portion of the product was purified by recrystallization from ethyl acetate.

NMR (DMSOd$_6$) 3.65 (s, 2, 2-CH$_2$), 3.91 (s, 3, tetrazole CH$_3$), 4.32 (s, 2, 3'-CH$_2$), 5.11 (d, 1, 6$\alpha$-H), 5.79 (indefinite quartet which changes to a sharp doublet when D$_2$O and trifluoroacetic acid are added, 1, 7$\alpha$-H), 6.12 (d, 1, CH or acetamido), 7.05, 7.30, and 7.62 (aromatic complex, 7, thienyl H and aromatic H of benzimidazole), and 8.81 and 9.60 ppm. (dd, each represents one amide H).

EXAMPLE 5

Employing the method of Example 3, 1.48 gms. (3 mmoles.) of 7-($\alpha$-amino-4-hydroxyphenylacetamido)-3-(5-methyl-1,3,4-thiadiazol-2-ylthiomethyl)-3-cephem-4-carboxylic acid were acylated in the presence of 2.37 gms. (18 mmoles.) of N-trimethylsilylacetamide (MSA) instead of BSA to obtain 211 mg. of 7-[$\alpha$-(benzimidazol- 2-ylcarbonylamino)-4-hydroxyphenylacetamido]-3-(5-methyl-1,3,4-thiadiazol-2-ylthiomethyl)-3-cephem-4-carboxylic acid.

NMR (DMSOd$_6$ and TFAd$_1$) 2.68 (s, 3, thiadiazole CH$_3$), 3.65 (s, 2, 2-CH$_2$), 4.39 (q, 2, 3'-CH$_2$), 5.07 (d, 1, 6α-H), 5.82 (s, 1, benzylic H; and d, 1, 7α-H), 7.16 (center of quartet, 4, aromatic H of p-hydroxyphenyl), and 7.73 ppm (aromatic complex, 4, aromatic H of benzimidazole).

EXAMPLE 6

Employing the method of Example 3, 536 mg. (1 mmole.) of 7-(α-amino-4-hydroxyphenylacetamido)-3-carbamoyloxymethyl-3-cephem-4-carboxylic acid were acylated in the presence of 0.91 gms. (7 mmoles.) of MSA instead of BSA to obtain 248 mg. of 7-[α-(benzimidazol-2-ylcarbonylamino)-4-hydroxyphenylacetamido]-3-carbamoyloxymethyl-3-cephem-4-carboxylic acid.

NMR (DMSOd$_6$) 3.42 (s, 2, 2-CH$_2$), 4.74 (d, 2, 3'-CH$_2$), 5.06 (d, 1, 6α-H), 5.72 (indefinite, but changes to a sharp singlet and a doublet when D$_2$O and TFAd$_1$ are added; each equals 1-H; 7α-H and benzylic H), 6.55 (s, 2, carbamate NH$_2$), 7.00 (center of quartet, 4, aromatic H of p-hydroxyphenyl), 7.49 (center of aromatic complex, 4, aromatic H of benzimidazole), and 8.74 and 9.42 ppm. (dd, each equals 1 H, amide H).

EXAMPLE 7

To 50 ml. of dry tetrahydrofuran were added 486 mg. (3 mmoles) of 2-benzimidazolecarboxylic acid and 459 mg. (3 mmoles) of 1-hydroxybenzotriazole. The mixture was stirred, and 618 mg. (3 mmoles) of N,N'-dicycolhexylcarbodiimide were added. The mixture was stirred for two hours at room temperature.

Separately, 1,90 grams (3 mmoles) of 7-(α-amino-4-hydroxyphenylacetamido)-3-(4-methyl-5-oxo-6-hydroxy-4,5-dihydro-1,2,4-triazin-3-ylthiomethyl)-3-cephem-4-carboxylic acid and 3.06 grams of N-trimethylsilylacetamide were stirred in dry tetrahydrofuran for about 1 hour and until solution was complete. The mixture from the above preparation of the 2-benzimidazolecarboxylic acid acylating agent was filtered, and the filtrate was added to the solution of the cephalosporin maintained at 0° C. The reaction mixture then was warmed to room temperature and was stirred for 4 hours. Methanol was added to the reaction mixture, and the resulting precipitate was filtered after stirring 10 minutes. The filtrate was evaporated to about 15 ml., and the concentrated mixture was dropped into stirring water. The pH of the mixture was lowered to 2.0 by addition of 1N hydrochloric acid. Ether was added, and the mixture was filtered. The solid was dried and was triturated with methylene chloride. The insolubles were filtered, dried, and dissolved in about 500 ml. of a 9:1 mixture of ethyl acetate and methanol. The solution was evaporated to about 30 ml. and was filtered. The collected solid was dried to obtain 440 mg. of 7-[α-(benzimidazol-2-ylcarbonylamino)-4-hydroxyphenylacetamido)-3-(4-methyl-5-oxo-6-hydroxy-4,5-dihydro-1,2,4-triazin-3-ylthiomethyl)-3-cephem-4-carboxylic acid.

NMR (DMSOd$_6$ and TFAd$_1$) 3.46 (s, 3, methyl on triazine), 3.61 (broad s, 2, 2-CH$_2$), 4.16 (broad s, 2, 3'-CH$_2$), 5.13 (d, 1, 6α-H), 5.81 (d, 1, 7α-H), 5.85 (s, 1, benzylic H), 7.12 (q, 4, aromatic H of p-hyroxyphenyl), and 7.75 (aromatic complex, 4, aromatic H of benzimidazole).

We claim:
1. A compound of the formula

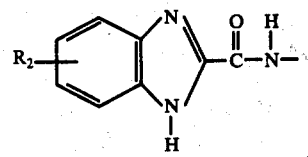

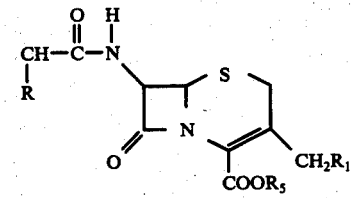

in which R is phenyl, monohydroxyphenyl, dihydroxyphenyl, monohalophenyl, monohydroxy substituted monohalophenyl, thienyl, or furyl;

R$_1$ is

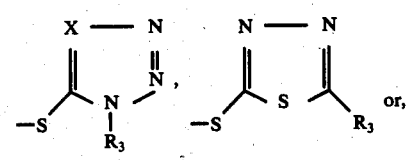

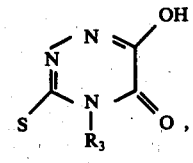

in which, in any of the above, X is =CH— or =N—, and R$_3$ is hydrogen or C$_1$–C$_4$ alkyl;

R$_2$ is hydrogen, C$_1$–C$_3$ alkyl, C$_1$–C$_3$ alkoxy, chloro, bromo, or fluoro; and R$_5$ is hydrogen, indanyl, phthalidyl, an acyloxymethyl group of the formula

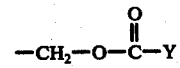

in which Y is C$_1$–C$_4$ alkyl or phenyl, or, when R$_5$ is hydrogen, the pharmaceutically acceptable non-toxic salts thereof.

2. Compound of claim 1, in which R$_2$ is hydrogen.
3. Compound of claim 2, in which R is phenyl.
4. Compound of claim 2, in which R is p-hydroxyphenyl.
5. Compound of claim 1, in which R$_1$ is

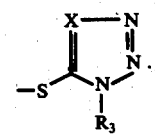

6. Compound of claim 5, in which X is =CH—.
7. Compound of claim 5, in which X is =N—.
8. Compound of claim 5, in which R$_3$ is hydrogen.
9. Compound of claim 5, in which R$_3$ is methyl.
10. Compound of claim 5, in which R is p-hydroxyphenyl.
11. Compound of claim 1, in which R$_1$ is

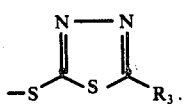
12. Compound of claim 11, in which $R_3$ is methyl.
13. Compound of claim 12, in which R is p-hydroxyphenyl.
14. Compound of claim 1, in which $R_1$ is
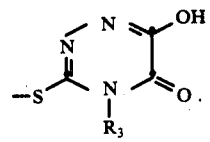
15. Compound of claim 14, in which $R_3$ is methyl.
16. Compound of claim 15, in which R is p-hydroxyphenyl.
* * * * *